United States Patent
Brannon et al.

(10) Patent No.: US 6,530,258 B2
(45) Date of Patent: Mar. 11, 2003

(54) DISK DRIVE LASER MELT BUMP DISK FOR ACCURATE GLIDE CALIBRATION AND CERTIFICATION PROCESSING

(75) Inventors: James Hammond Brannon, Palo Alto, CA (US); Shanlin Duan, Fremont, CA (US); Yu Lo, Fremont, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/911,147

(22) Filed: Jul. 23, 2001

(65) Prior Publication Data

US 2003/0015018 A1 Jan. 23, 2003

(51) Int. Cl.$^7$ .............................................. G01B 21/30
(52) U.S. Cl. .......................... 73/1.89; 73/1.181; 65/105
(58) Field of Search ................................ 73/1.89, 1.81; 65/105

(56) References Cited

U.S. PATENT DOCUMENTS

| | | | | |
|---|---|---|---|---|
| 4,833,001 A | * | 5/1989 | Kijima et al. | 65/31 |
| 5,567,484 A | * | 10/1996 | Baumgart et al. | 427/555 |
| 5,675,462 A | | 10/1997 | Ayabe | |
| 5,741,560 A | * | 4/1998 | Ross | 427/555 |
| 5,847,823 A | * | 12/1998 | Imaino et al. | 356/243 |
| 5,863,473 A | | 1/1999 | Ohsawa et al. | |
| 5,912,791 A | | 6/1999 | Sundaram et al. | |
| 5,956,217 A | | 9/1999 | Xian et al. | |
| 5,978,189 A | | 11/1999 | Habu | |
| 6,117,620 A | | 9/2000 | Imaino et al. | |
| 6,140,814 A | | 10/2000 | Sundaram | |
| 6,164,118 A | | 12/2000 | Suzuki et al. | |

FOREIGN PATENT DOCUMENTS

| | | | |
|---|---|---|---|
| JP | 245322 | * | 10/1991 |
| JP | 8124340 | | 5/1996 |
| JP | 9106538 | | 4/1997 |
| JP | 213387 | * | 8/1999 |

* cited by examiner

*Primary Examiner*—Daniel S. Larkin
*Assistant Examiner*—Nashmiya Fayyaz
(74) *Attorney, Agent, or Firm*—Robert B. Martin; Bracewell & Patterson, L.L.P.

(57) ABSTRACT

A bump disk for accurate glide calibration has a new type of glass laser melt bumps that give the same signal amplitudes as conventional AlMg laser melt bumps for the same bump height. The present invention provides a solution to switch the calibration bumps from AlMg to glass, and can be used in disk manufacturing lines to save 30% on the cost of hard disks from inaccurate glide certification processes. The solution is to trim or burnish away loose and/or high particles on production disks before the glide tests. This additional processing step causes the responses from the glass bumps to become very similar to those of the AlMg bumps, thereby enabling glass and AlMg disks to become materially compatible.

7 Claims, 2 Drawing Sheets

DISK DRIVE LASER MELT BUMP DISK FOR ACCURATE GLIDE CALIBRATION AND CERTIFICATION PROCESSING

BACKGROUND OF THE INVENTION

1. Technical Field

The present invention relates in general to improved disk certification calibration, and in particular to an improved disk drive laser melt bump disk for accurate glide calibration.

2. Description of the Related Art

Generally, a data access and storage system consists of one or more storage devices that store data on magnetic or optical storage media. For example, a magnetic storage device is known as a direct access storage device (DASD) or a hard disk drive (HDD) and includes one or more disks and a disk controller to manage local operations concerning the disks. The hard disks themselves are usually made of aluminum alloy or a mixture of glass and ceramic, and are covered with a magnetic coating. Typically, two or three disks are stacked vertically on a common spindle that is turned by a disk drive motor at several thousand revolutions per minute (rpm).

The only other moving part within a typical HDD is the actuator assembly. The actuator moves magnetic read/write heads to the desired location on the rotating disk so as to write information to or read data from that location. Within most HDDs, the magnetic read/write head is mounted on a slider. A slider generally serves to mechanically support the head and any electrical connections between the head and the rest of the disk drive system. The slider is aerodynamically shaped to glide over moving air in order to maintain a uniform distance from the surface of the rotating disk, thereby preventing the head from undesirably contacting the disk.

Typically, a slider is formed with an aerodynamic pattern of protrusions (air bearing design) on its air bearing surface (ABS) that enables the slider to fly at a constant height close to the disk during operation of the disk drive. A slider is associated with each side of each platter and flies just over the platter's surface. Each slider is mounted on a suspension to form a head gimbal assembly (HGA). The HGA is then attached to a semi-rigid actuator arm that supports the entire head flying unit. Several semi-rigid arms may be combined to form a single movable unit having either a linear bearing or a rotary pivotal bearing system.

The head and arm assembly is linearly or pivotally moved utilizing a magnet/coil structure that is often called a voice coil motor (VCM). The stator of a VCM is mounted to a base plate or casting on which the spindle is also mounted. The base casting with its spindle, actuator VCM, and internal filtration system is then enclosed with a cover and seal assembly to ensure that no contaminants can enter and adversely affect the reliability of the slider flying over the disk. When current is fed to the motor, the VCM develops force or torque that is substantially proportional to the applied current. The arm acceleration is therefore substantially proportional to the magnitude of the current. As the read/write head approaches a desired track, a reverse polarity signal is applied to the actuator, causing the signal to act as a brake, and ideally causing the read/write head to stop directly over the desired track.

The presence of asperities on the surfaces of the disks can have a deleterious effect on the performance of disk drives. For this reason, a glide test is performed on finished disks to detect asperities that might contact the magnetic head flying at its normal height in a disk drive. In the test, a special glide head containing a piezoelectric transducer (PZT) is flown over a disk at an altitude or height that is below the normal drive fly height. Glide head contact with an asperity creates a PZT voltage response that generally scales with increasing size of the asperity. If the voltage response exceeds a predetermined level, the disk is rejected. As such, quantitative glide testing requires calibration of the voltage response with respect to asperity height.

One method of calibrating glide heads uses laser-generated, nano-sized protrusions or laser melt bumps (LMB) on the surface of a disk that can serve as calibration asperities. Laser nano-bump generation is a technique that is used throughout the data storage industry. Flying a guide head over a laser nano-bump whose height is known (e.g., by interference or atomic force microscopy) will thus generate a calibrated PZT response. However, the certainty of the response is much improved by use of statistical averaging methods.

Since the glide certification process is one of the most important steps in fabricating the hard disks of the disk drives, the accuracy of glide certification is the single most important factor that directly affects the yield and, thus, the production is cost of the disks. Prior to the glide certification process on production disks, glide heads are calibrated by flying over the LMB with certain interference heights. Currently, the LMB are made on aluminum-magnesium (AlMg) substrates.

An enlarged isometric view of a single prior art AlMg bump 11 is depicted in FIG. 1. As is typical of AlMg bumps, the perimeter 13 of bump 11 rises slightly above the planar surface of the AlMg disk 15, while the center of bump 11 is a relatively deep parabolic recess 17. Unfortunately, there is a material incompatibility for calibration on AlMg substrates and tests performed on other materials. Moreover, the supply of AlMg substrates used for calibration bump disks in disk manufacturing engineering is limited, such that there is an urgent need to switch all calibration devices from AlMg to another material. Thus, an improved bump disk for accurate glide calibration is needed.

SUMMARY OF THE INVENTION

One embodiment of an improved bump disk for accurate glide calibration has a new type of glass laser melt bumps that give the same signal amplitudes as conventional AlMg laser melt bumps for the same bump height. The present invention provides a solution to switch the calibration bumps from AlMg to glass, and can be used in disk manufacturing lines to save 30% on the cost of hard disks from inaccurate glide certification processes. The solution is to trim or burnish away the very top portion (i.e., the low response portion) of the glass bumps. This additional processing step causes the responses from the glass bumps to become very similar to those of the AlMg bumps, thereby enabling glass and AlMg disks to become materially compatible.

The foregoing and other objects and advantages of the present invention will be apparent to those skilled in the art, in view of the following detailed description of the preferred embodiment of the present invention, taken in conjunction with the appended claims and the accompanying drawings.

BRIEF DESCRIPTION OF THE DRAWINGS

So that the manner in which the features, advantages and objects of the invention, as well as others which will become apparent, are attained and can be understood in more detail, more particular description of the invention briefly summarized above may be had by reference to the embodiment thereof which is illustrated in the appended drawings, which drawings form a part of this specification. It is to be noted, however, that the drawings illustrate only a preferred embodiment of the invention and is therefore not to be considered limiting of its scope as the invention may admit to other equally effective embodiments.

DETAILED DESCRIPTION OF THE PREFERRED EMBODIMENT OF THE PRESENT INVENTION

Figure 3:
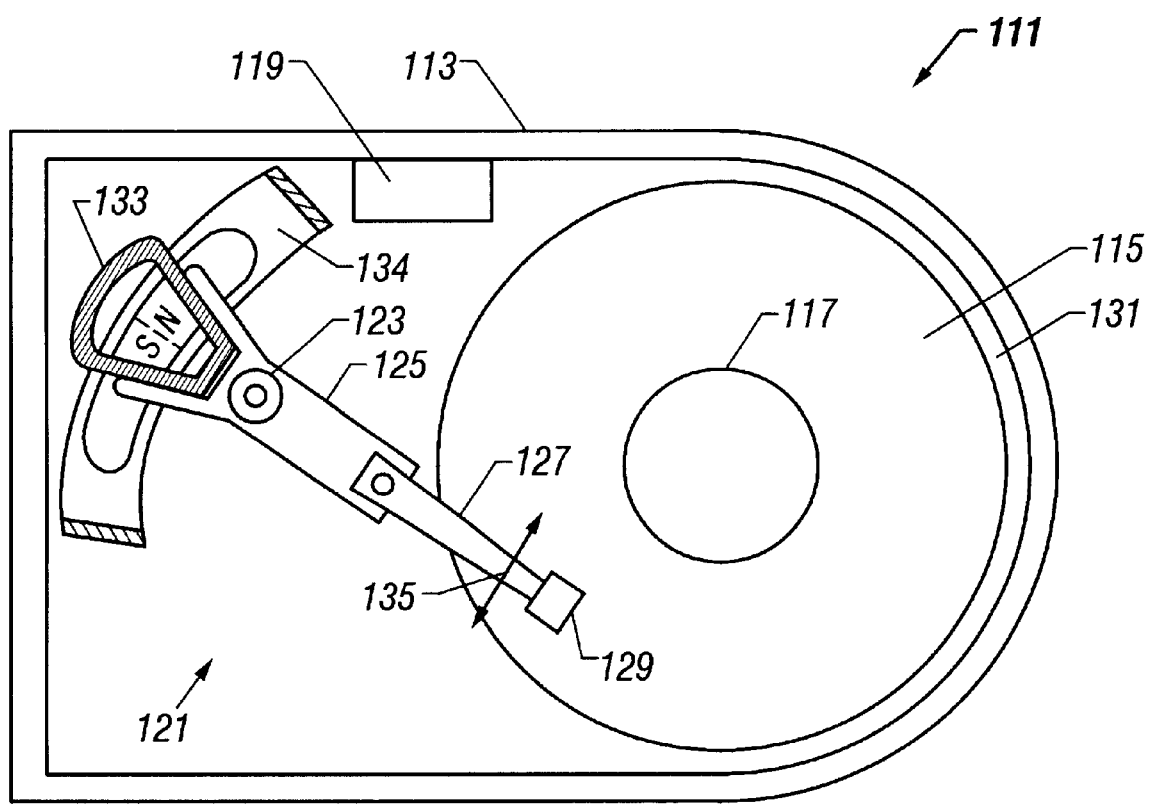
FIG. 3 is a plan view of a disk drive assembly with a cover removed to show the principle subassembly.

Referring to FIG. 3, a schematic drawing of one embodiment of an information storage system comprising a magnetic hard disk file or drive 111 for a computer system is shown. Drive 111 has an outer housing or base 113 containing a plurality of stacked, parallel magnetic disks 115 (one shown) which are closely spaced apart and formed from disk substrates. Disks 115 are rotated by a spindle motor assembly 131 having a central drive hub 117. An actuator 121 comprises a plurality of stacked, parallel actuator arms 125 (one shown) in the form of a comb that is pivotally mounted to base 113 about a pivot assembly 123. A controller 119 is also mounted to base 113 for selectively moving the comb of arms 125 relative to disks 115.

In the embodiment shown, each arm 125 has extending from it at least one cantilevered load beams or suspensions 127, a magnetic read/write transducer or head 129 mounted on a slider secured to a flexure that is flexibly mounted to each suspension 127. The read/write heads 129 magnetically read data from and/or magnetically write data to disks 115. The level of integration called head gimbal assembly is head 129 and the slider are mounted on suspension 127. Suspensions 127 have a spring-like quality which biases or urges the slider against the disk to enable the creation of the air bearing film between the slider and disk surface. A voice coil 133 housed within a conventional voice coil motor magnet assembly 134 (top pole not shown) is also mounted to arms 125 opposite the head gimbal assemblies. 25 Movement of the actuator 121 (indicated by arrow 135) by controller 119 moves head gimbal assemblies 129 radially across tracks on the disks 115 until the heads 129 settle on the target tracks. The head gimbal assemblies operate in a conventional manner and always move in unison with one another, unless drive 111 uses multiple independent actuators (not shown) wherein the arms can move independently of one another.

Figure 1:
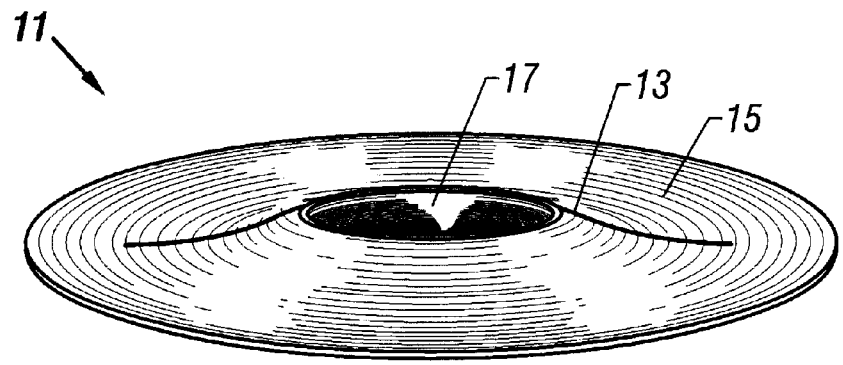
FIG. 1 is an enlarged isometric view of a conventional AlMg disk substrate with laser melt bumps.
Figure 2:
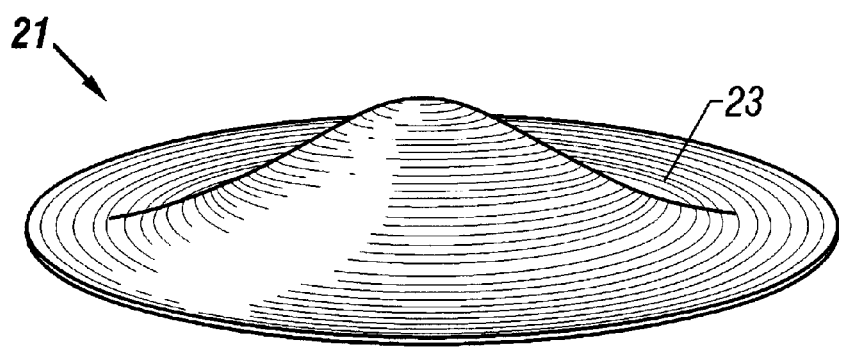
FIG. 2 is an enlarged isometric view of a glass disk substrate with laser melt bumps.

As shown in FIG. 2, a glass disk 23 has glass bumps 21 (one shown) with a large, smooth, rounded protrusion that extends entirely above the surface of the glass disk 23. These shapes are very different from those of prior art AlMg disks. The difference in shape is due to the different materials used to form the disks and to the differences in laser wavelength, laser pulse duration, and laser intensity.

However, for the same bump height, glass bumps show 30% lower piezoelectric transducer (PZT) signal amplitudes as compared to those made on AlMg with the same height.

The low calibration amplitude problem directly impacts the accuracy of the glide test and the resulting "qualification glide height" for the products. A 30% drop in signal amplitude during calibration can be read as a 30% drop in the yield of fabricated hard disks, which can be translated into a 30% increase in the cost of hard disks. These factors would tend to cause disk manufacturers to strongly hesitate (i.e., teach away) from switching from AlMg to glass.

Figure 4:
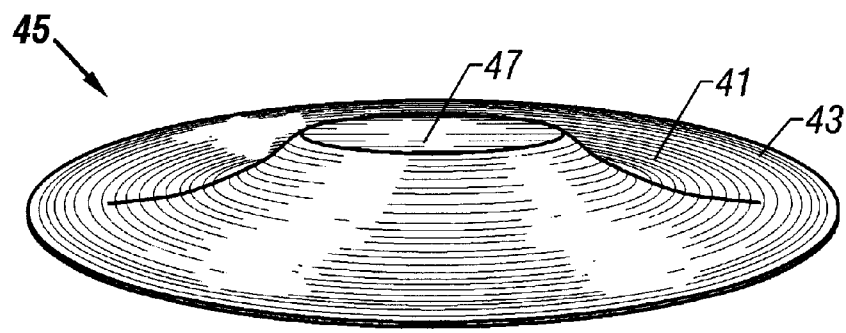
FIG. 4 is an enlarged isometric view of one embodiment of a glass disk substrate with laser melt bumps constructed in accordance with the present invention.

Referring now to FIG. 4, the surface 41 of a glass disk substrate 43 used to form disk 115 is shown. Substrate 43 has a large number of rounded glass protrusions or bumps 45 (one shown) that are initially formed by the laser melt bump process previously described. However, after bumps 45 are formed they are trimmed or burnished in a subsequent processing step. In this latter step, bumps 45 are reduced at their outermost or distal portions to form a generally level peak 47, which is substantially parallel to surface 41.

The trimming of bumps 45 is preferably done with a burnish head, which is usually used to "burnish" away loose and high particles on production disks before the glide tests. By comparing glass bumps before and after burnishing (approximately 20 steps of burnishing), the "tail" of the spindown curves (fly height vs. amplitude) are trimmed away and the responses from the glass bumps are very similar to AlMg bumps. After this processing step, peaks 47 are essentially flat and the debris accumulates adjacent to the bumps 45. The debris is removed during subsequent processing.

This subtle modification to bumps produces significant and unexpected results. Glass bumps 45 yield the same signal amplitudes as the prior AlMg bumps for the same bump height. Thus, the present invention provides a solution for the long felt need to switch the calibration bumps from AlMg to glass. This process can be used in manufacturing lines and save approximately 30% of the cost of hard disks as compared to the relatively inaccurate glide certification processes of the prior art.

Hundreds of glass bumps of different heights, size, and glass materials have been tested by glide. The signal sensitivity of AlMg substrates can be achieved with glass substrates modified in accordance with the present invention. A calculation of cross-sectional area versus bump height supports these experimental findings. In addition, the area curves for glass bumps suggest that the AlMg area curves can be achieved by trimming off the top portion of bumps 45.

While the invention has been shown or described in only some of its forms, it should be apparent to those skilled in the art that it is not so limited, but is susceptible to various changes without departing from the scope of the invention.

What is claimed is:

1. A bump disk for accurate glide calibration, comprising:

a glass substrate;

calibration laser melt bumps formed on the glass substrate; and a distal portion of each of the calibration laser melt bumps is trimmed; and wherein the distal portions of the laser melt bumps are flat.

2. The bump disk of claim 1 wherein the distal portions of the laser melt bumps are burnished.

3. The bump disk of claim 1 wherein the distal portions of the laser melt bumps are substantially parallel to a surface of the glass substrate.

4. A disk drive bump disk for accurate glide calibration, comprising:

a glass substrate;

calibration laser melt bumps formed on the glass substrate; and a flat distal portion on each of the calibration laser melt bumps is burnished substantially parallel to a surface of the glass substrate.

5. A method of fabricating a bump disk for accurate glide calibration, comprising:

(a) providing a glass substrate;

(b) forming laser melt bumps on the glass substrate; and (c) trimming distal portions of the laser melt bumps into flat surfaces.

6. The method of claim 5 wherein step (c) comprises burnishing the distal portions of the laser melt bumps.

7. The method of claim 5 wherein step (c) comprises forming the distal portions of the laser melt bumps parallel to a surface of the glass substrate.

* * * * *

UNITED STATES PATENT AND TRADEMARK OFFICE
CERTIFICATE OF CORRECTION

PATENT NO.   : 6,530,258 B1
DATED        : March 11, 2003
INVENTOR(S)  : Brannon et al.

It is certified that error appears in the above-identified patent and that said Letters Patent is hereby corrected as shown below:

<u>Column 4,</u>
Line 62, replace "flat" with -- flat, so as to be used for glide calibration. --

<u>Column 5,</u>
Line 9, replace the entire claim with:
-- A method of fabricating a bump disk for accurate glide calibration, comprising:
(a) providing a glass substrate:
(b) forming calibration laser melt bumps on the glass substrate; and
(c) trimming distal portions of the calibration laser melt bumps into flat surfaces, so as to be used for glide calibration. --

<u>Column 6,</u>
Line 9, "substrate" should read -- substrate, so as to be used for glide calibration --.

Signed and Sealed this

Thirtieth Day of September, 2003

JAMES E. ROGAN
*Director of the United States Patent and Trademark Office*